(12) United States Patent
Iwasaki et al.

(10) Patent No.: US 6,703,031 B1
(45) Date of Patent: Mar. 9, 2004

(54) CYSTEINE DERIVATIVES

(75) Inventors: Keiji Iwasaki, Kawasaki (JP); Manabu Kitazawa, Kawasaki (JP); Eiji Shiojiri, Kawasaki (JP); Kazutami Sakamoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/806,937

(22) PCT Filed: Oct. 8, 1999

(86) PCT No.: PCT/JP99/05584

§ 371 (c)(1),
(2), (4) Date: Jun. 14, 2001

(87) PCT Pub. No.: WO00/21925

PCT Pub. Date: Apr. 20, 2000

(30) Foreign Application Priority Data

Oct. 9, 1998 (JP) .......................................... 10-287615

(51) Int. Cl.[7] ........................ A61K 7/00; A61K 31/16; A01N 25/00; C07C 237/00
(52) U.S. Cl. ...................... 424/401; 514/613; 514/844; 514/847; 564/197; 564/198
(58) Field of Search ................. 514/804, 613, 514/847; 564/197, 198; 424/401

(56) References Cited

U.S. PATENT DOCUMENTS

| 4,441,976 A | 4/1984 | Iemmi et al. |
| 4,708,965 A | 11/1987 | Morgan |
| 4,724,239 A | 2/1988 | Morgan |
| 4,827,016 A | 5/1989 | Morgan |
| 4,918,196 A | * 4/1990 | Doya et al. |
| 5,441,976 A | 8/1995 | Andersson et al. |
| 5,780,508 A | 7/1998 | Andersson et al. |

FOREIGN PATENT DOCUMENTS

| EP | 0 300 100 | 1/1989 |
| EP | 0727207 A1 * | 6/1991 |
| EP | 0 463 514 | 1/1992 |
| GB | 22 00 633 | 8/1988 |
| JP | 1-256586 | 10/1989 |
| JP | 03188011 A * | 8/1991 |
| JP | 11269051 A * | 10/1999 |
| WO | WO 90/14429 A1 * | 11/1990 |

OTHER PUBLICATIONS

A.S. Baldwin, Jr., *The Journal of Clinical Investigation*, vol. 107, No. 1, pp. 3–6, 2001.
Y. Yamamoto, et al., *The Journal of Clinical Investigation*, vol. 107, No. 2, pp. 135–142, 2001.
H.–Y. Chung, et al., "The Inflammation Hypothesis of Aging", in *Annals of New York Academy of Science*, vol. 928, pp. 327–335, 2001.
H.–Y. Chung, et al., *Mechanisms of Ageing and Development*, vol. 111, pp. 97–106, 1999.
V. Chechik, et al., Langmuir, vol. 14, No. 11, pps. 3003–3010, "Self–Assembled Monolayers of Branched Thiols and Disulfides on Gold: Surface Coverage, Order and Chain Orientation," 1998.
T. C. Manh, et al., Int. J. Biol. Macromol., vol. 6, No. 1, pps. 13–20, "Experimental Study on Aggregation of Model Monopeptide Molecules: 6. A Model for Peptide .Beta.–Structures?," 1984.

* cited by examiner

Primary Examiner—Johann Richter
Assistant Examiner—Paul A. Zucker
(74) Attorney, Agent, or Firm—Oblon, Spivak, McClelland, Maier & Neustadt, P.C.

(57) ABSTRACT

Objects of the present invention are to provide an oxidative stress inhibitor which is capable of suppressing the expression of a cytotoxic protein and the activation of a gene transcriptional regulatory factor taking part such expression of a cytotoxic protein and exhibits good feeling upon use and safety; to provide a method for preventing, retarding, alleviating or treating a skin change due to aging or an undesirable aesthetic skin change, both caused or promoted by an oxidative stress; and to provide a cosmetic composition or dermatologic preparation for external use comprising the oxidative stress inhibitor as an effective ingredient, and for those purposes are employed an oxidative stress inhibiting agent which comprises, as an effective ingredient, at least one selected from cysteine or cystine derivatives and the salts thereof.

29 Claims, No Drawings

US 6,703,031 B1

CYSTEINE DERIVATIVES

This application is a 371 of PCT/JP99/05584, filed on Oct. 8, 1999.

TECHNICAL FIELD

The present invention relates to an oxidative stress inhibitor useful for prevention, retardation, alleviation or treatment of diseases or dermal injuries or diseases caused by an oxidative stress; a method for inhibiting an oxidative stress by using such an oxidative stress inhibitor; and a cosmetic composition or dermatologic preparation for external use which comprises such an oxidative stress inhibitor as an effective ingredient.

BACKGROUND ART

In recent years, causes of diseases or dermal injuries or diseases brought about by an oxidative stress such as ultraviolet rays, active oxygen, free radicals or the like have been searched briskly. For example, it is known that cytotoxic cytokines such as IL-1α, TNF-α and the like or extracellular matrix proteases such as collagenase and the like are closely related to aging, canceration or malignant alteration, edema, pigmentation or the like as its cause (for example, "Oxidative Stress in Dermatology", Marcel Dekker, Inc., pp. 187–205, 1993). Expression of a gene coding for such a protein is mainly controlled at the level of genetic transcription, whereas, regarding cytotoxic proteins such as cytotoxic cytokines and extracellular matrix proteases, it is controlled by a transcriptional regulatory factor such as NF-κB or AP-1 (for example, "Active oxygen and Signal transmission", Kodansha Scientific, pp. 37–46, 1996). In practice, NF-κB and AP-1 are known to be activated by an oxidative stress and promote the expression of cytotoxic protein (for example, "Active oxygen and Signal transmission", Kodansha Scientific, pp. 1–20, 1996). Diseases or dermal injuries or diseases caused by an oxidative stress are therefore expected to be prevented, retarded, alleviated or treated if it becomes possible to suppress the activation of NF-κB or AP-1 due to an oxidative stress.

There is a description that the activation of NF-κB is inhibited by a sulfur-containing antioxidant such as N-acetyl-L-cysteine or pyrrolidine dithiocarbamate (for example, "Active oxygen and Signal transmission", Kodansha Scientific, pp. 37–46, 1996). It is reported that N-acetyl-L-cysteine can also suppress the activation of AP-1 (for example, "FEBS Letters", Vol. 384, pp. 92–96, 1996). These compounds are, however, accompanied with such drawbacks as insufficient effects or strong cytotoxicity. Sulfur-containing compounds such as N,N'-diacetyl-L-cystine are known to suppress dermal inflahmmation induced by leukotrienes (ex. U.S. Pat. No. 4,827,016), but not known to inhibit cytokines or transcription factor taking part in aging, canceration, edema, pigmentation or the like. In addition to sulfur-containing antioxidants, there are reports on retinoic acid used for inhibiting the activation of AP-1 and the expression of extracellular matrix proteases (for example, "Nature", Vol. 379, pp. 335–339, 1996); and steroidal anti-inflammatory drugs or non-steroidal anti-inflammatory drugs used for suppressing the activation of NF-κB (for example, "Bio Essays", Vol. 18, pp. 373–378, 1996). Retinoic acid and steroidal anti-inflammatory drugs are not free from side effects such as detachment of the skin and steroid-induced skin diseases, respectively, so that they cannot be used freely. Non-steroidal anti-inflammatory drugs do not cause systemic side effects which are observed upon use of a steroidal anti-inflammatory drug, but there is room for improvement in its local side effects. In addition, its effects for suppressing the activation of inflammatory factors are insufficient.

As one of the diseases or dermal injuries or diseases caused by an oxidative stress, a change in the skin due to aging or an undesirable esthetic change in the skin can be mentioned. It is reported that in order to prevent or retard such a change, a natural extract having action for alleviating skin roughness or the component contained therein, such as astaxantin, and a cystine derivative are in combination applied to the skin (for example, Japanese Patent Application Laid-Open: (Kokai) No. Hei 9-143,063). According to the report, such a combination contributes to the recovery of resilience or luster of the skin or the amelioration of the somber coloring,-but does not exhibit sufficient effects. In addition, its effects against skin wrinkles or flabby skin, the most eminent symptoms in the observation of the aged skin, are, however, not revealed.

Induction or promotion of skin wrinkles or flabby skin is a typical example of skin change due to aging or an undesirable aesthetic skin change, both brought about by an oxidative stress. The sun light or ultraviolet rays therefrom can be mentioned as its cause (for example, "Shin Keshohin-gaku", Nanzando, pp. 38–46, 1993). As a method for preventing or retarding such a change, application of an antioxidant such as tocopherol, ascorbic acid, N-acetyl-L-cysteine or the like to the kin is reported (for example, "Photodermatol. Photoimmunol. Photomed., Vol.7, pp. 56–62, 1990 or Japanese Language Laid-Open Publication (PCT) No. Hei 6-510,542). Prevention or retardation is also effected by the application of an anti-inflammatory drug or an ultraviolet absorber, other than an antioxidant (for example, "Photodermatol. Photoimmunol. Photomed., Vol.7, pp. 153–158, 1990 or J. Photochem. Photobiol. B: Biol., Vol. 9, pp. 323–334, 1991) or improvement is conducted using retinoic acid (for example, "J. Invest. Dermatol., Vol. 98, pp. 248–254, 1992). These compounds are, however, accompanied with the problems such as insufficient effects, strong cytotoxicity and low light stability. Moreover, anti-inflammatory drugs and retinoic acid are not free from side effects as described above.

DISCLOSURE OF THE INVENTION

Objects of the present invention are to provide, based on the above-described background art, an oxidative stress inhibitor which is capable of suppressing the activation of a gene transcriptional regulatory factor taking part in the expression of a cytotoxic protein and exhibits good feeling upon use and safety; to provide a method for preventing, retarding, alleviating or treating a skin change due to aging or an undesirable aesthetic skin change, both caused or promoted by an oxidative stress; and to provide a cosmetic composition or dermatologic preparation for external use comprising the oxidative stress inhibitor as an effective ingredient.

The present inventors have proceeded with an extensive investigation with a view toward attaining the above-described objects. As a result, they have found that the above-described objects can be attained by using a cysteine or cystine derivative represented by the below-described general formula (I), (II) or (III) or a salt thereof as an effective ingredient; or by using a cysteine or cystine derivative represented by the below-described general formula (IV) or a salt thereof and an antioxidant, anti-inflammatory drug or ultraviolet absorber in combination. Based on these findings, the present invention has been completed.

Accordingly, the present invention relates to an oxidative stress inhibitor which comprises as an effective ingredient at least one selected from the cysteine or cystine derivatives represented by the below-described general formula (I) and the salts thereof.

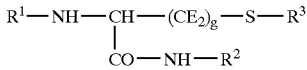
(I)

In the above-described general formula (I), $R^1$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms; the two E's represent, each independently, a hydrogen atom or an alkyl group having 1–6 carbon atoms, and g stands for an integer of 0 to 5, while $R^2$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^1$ represents a hydrogen atom or an acyl group having 2–3 carbon atoms, $R^2$ represents an alkyl group having 6–22 carbon atoms, a hydroxyalkyl group having 1–22 carbon atoms or a 3-alkoxy-2-hydroxypropyl group whose alkoxyl group has 1–22 carbon atoms. $R^3$ represents a hydrogen atom, an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atom or a group represented by the following general formula (1).

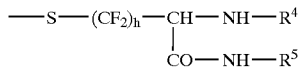
(1)

In the above-described general formula (1), $R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms; the two F's represent, each independently, a hydrogen atom or an alkyl group having 1–6 carbon atoms, and h stands for an integer of 0 to 5, while $R^5$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^4$ represents a hydrogen atom or an acyl group having 2–3 carbon atoms, $R^5$ represents an alkyl group having 6–22 carbon atoms, a hydroxyalkyl group having 1–22 carbon atoms or a 3-alkoxy-2-hydroxypropyl group whose alkoxyl group has 1–22 carbon atoms.

The cysteine or cystine derivatives represented by the above-described general formula (I) are not known in the literature, and therefore, are new compounds. Accordingly, the present invention relates also to the cysteine or cystine derivatives represented by the above-described general formula (I) and the salts thereof per se.

The present invention relates also to an oxidative stress inhibitor which comprises as an effective ingredient at least one selected from the cystine derivatives represented by the below-described general formula (II) and the salts thereof.

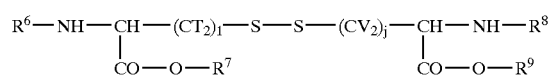
(II)

In the above-described general formula (II), $R^6$ and $R^8$ represent a hydrogen atom, an aminocarbonyl group, an acyl. group having 2–22 carbon-atoms, an alkyl group having 1–22 carbon atoms, a hydroxyalkyl group having 1–22 carbon atoms or a 3-alkoxy-2-hydroxypropyl group whose alkoxyl group has 1–22 carbon atoms; the two T's and the two V's represent, each independently, a hydrogen atom or an alkyl group having 1–6 carbon atoms, and i and j stand, each independently, for an integer of 0 to 5, while $R^7$ and $R^9$ represent a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^6$ and $R^8$ represent a hydrogen atom or an acyl group having 2 carbon atoms, and i and j are each 1, $R^7$ and $R^9$ represent an alkyl group having 2–22 carbon atoms, a hydroxyalkyl group having 1–22 carbon atoms or a 3-alkoxy-2-hydroxypropyl group whose alkoxyl group has 1–22 carbon atoms.

Also, the present invention relates to a preventing and/or treating agent for oxidative stress-induced diseases, inter alia, ultraviolet rays-induced diseases, which agent comprises at least one selected from the cysteine or cystine derivatives represented by the above-described general formula (I) or (II) and the salts thereof.

Furthermore, the present invention relates to a cosmetic additive to be added as a component to a cosmetic composition, which additive consists of at least one selected from the cysteine or cystine derivatives represented by the above-described general formula (I) or (II) and the salts thereof.

Still furthermore, the present invention relates to a cosmetic composition or a dermatologic preparation for external use which comprises at least one selected from the cysteine or cystine derivatives represented by the above-described general formula (I) or (II) and the salts thereof. The cosmetic composition of the present invention is useful for preventing or alleviationg oxidative stress-induced dermal injuries, and the dermatologic preparation for external use of the present invention is useful for preventing or treating oxidative stress-induced diseases.

Furthermore, the present invention relates to a method for preventing, retarding, alleviating or treating a skin change due to aging or an undesirable aesthetic skin change, both caused or promoted by an oxidative stress, which method comprises applying onto the skin a cosmetic composition or a dermatologic preparation for external use comprising, as an effective ingredient, at least one selected from the cysteine or cystine derivatives represented by the above-described general formula (I) or the below-described general formula (III) and the salts thereof.

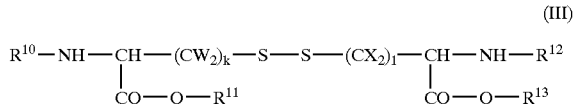
(III)

In the above-described general formula (III), $R^{10}$ and $R^{12}$ represent a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms; the two W's and the two X's represent, each independently, a hydrogen atom or an alkyl group having 1–6 carbon atoms, and k and l stand, each independently, for an integer of 0 to 5, while $R^{11}$ and $R^{13}$ represent a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^{10}$ and $R^{12}$ represent a hydrogen atom or an acyl group having 2 carbon atoms, and k and l are each 1, $R^{11}$ and $R^{13}$ represent an alkyl group having 1–22 carbon atoms, a hydroxyalkyl group having 1–22 carbon atoms or a 3-alkoxy-2-hydroxypropyl group whose alkoxyl group has 1–22 carbon atoms.

Moreover, the present invention relates to a cosmetic composition or a dermatologic preparation for external use which comprises Component (A) and Component (B), each described below.

Component (A): At least one selected from the cysteine or cystine derivatives represented by the below-described general formula (IV) and the salts thereof.

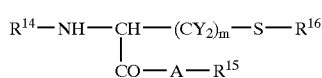

(IV)

In the above-described general formula (IV), $R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms; the two Y's represent, each independently, a hydrogen atom or an alkyl group having 1–6 carbon atoms, and m stands for an integer of 0 to 5, while A represents —O— or —NH—, $R^{15}$ represents a hydrogen atom, an alkyl group having 1–22 carbon atoms, a hydroxyalkyl group having 1–22 carbon atom or a 3-alkoxy-2-hydroxypropyl group whose alkoxyl group has 1–22 carbon atoms, and $R^{16}$ represents a hydrogen atom, an aminocarbonyl group an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms, or a group represented by the below-described general formula (2), with the proviso that when $R^{14}$ represents a hydrogen atom or when $R^{14}$ represents an aminocarbonyl group or an acyl group having 2 carbon atoms and A represents —O—, $R^{15}$ represents an alkyl group having 1–22 carbon atoms, a hydroxyalkyl group having 1–22 carbon atoms or a 3-alkoxy-2-hydroxypropyl group whose alkoxyl group has 1–22 carbon atoms.

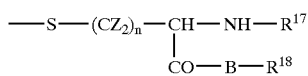

(2)

In the above-described general formula (2), $R^{17}$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms; the two Z's represent, each independently, a hydrogen atom or an alkyl group having 1–6 carbon atoms, and n stands for an integer of 0 to 5, while B represents —O— or —NH—, and $R^{18}$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^{17}$ represents a hydrogen atom or when $R^{17}$ represents an aminocarbonyl group or an acyl group having 2 carbon atoms and B represents —O—, $R^{18}$ represents an alkyl group having 1–22 carbon atoms, a hydroxyalkyl group having 1–22 carbon atoms or a 3-alkoxy-2-hydroxypropyl group whose alkoxyl group has 1–22 carbon atoms.

Component (B): At least one selected from an antioxidant, anti-inflammatory drug and ultraviolet absorbor.

Hereinbelow will be described the present invention in greater detail.

First, specific examples of the compounds relating to the present invention will be described.

In the cysteine or cystine derivative represented by the above-described general formula (I), (II), (III) or (IV), or the salts thereof, as $R^1$, $R^4$, $R^6$, $R^8$, $R^{10}$, $R^{12}$, $R^{14}$ and $R^{17}$, there may be mentioned hydrogen atom and aminocarbonyl, acetyl, propionyl, isopropionyl, n-butyryl, isobutyryl, sec-butyryl, tert-butyryl, n-valeryl, sec-valeryl, pivaloyl, isovaleryl, n-hexanoyl, cyclohexanoyl, n-heptanoyl, n-octanoyl, 2-ethylhexanoyl, nonanoyl, isononanoyl, decanoyl, isodecanoyl, undecanoyl, lauroyl, tridecanoyl, isotridecanoyl, myristoyl, palmitoyl, isopalmitoyl, stearoyl, isostearoyl, oleoyl, docosanoyl, methyl, ethyl, propyl, isopropyl, n-butyl, isobutyl, sec-butyl, tert-butyl, n-amyl, sec-amyl, tert-amyl, isoamyl, n-hexyl, cyclohexyl, n-heptyl, n-octyl, 2-ethylhexyl, nonyl, isononyl, decyl, isodecyl, undecyl, lauryl, tridecyl, isotridecyl, myristyl, cetyl, isocetyl, stearyl, isostearyl, oleyl, behenyl, 2-hydroxyethyl, 2-hydroxypropyl, 2-hydroxyisopropyl, 2-hydroxy-n-butyl, 2-hydroxyisobutyl, 2-hydroxy-sec-butyl, 2-hydroxy-tert-butyl, 2-hydroxy-n-amyl, 2-hydroxy-sec-amyl, 2-hydroxy-tert-amyl, 2-hydroxyisoamyl, 2-hydroxy-n-hexyl, 2-hydroxycyclohexyl, 2-hydroxy-n-heptyl, 2-hydroxy-n-octyl, 2-hydroxy-2-ethylhexyl, 2-hydroxynonyl, 2-hydroxyisononyl, 2-hydroxydecyl, 2-hydroxyisodecyl, 2-hydroxyundecyl, 2-hydroxylauryl, 2-hydroxytridecyl, 2-hydroxyisotridecyl, 2-hydroxymyristyl, 2-hydroxycetyl, 2-hydroxyisocetyl, 2-hydroxystearyl, 2-hydroxyisostearyl, 2-hydroxyoleyl, 2-hydroxybehenyl, 3-methoxy-2-hydroxypropyl, 3-ethoxy-2-hydroxypropyl, 3-propoxy-2-hydroxypropyl, 2-isopropoxy-2-hydroxypropyl, 3-n-butoxy-2-hydroxypropyl, 3-isobutoxy-2-hydroxypropyl, 3-sec-butoxy-2-hydroxypropyl, 3-tert-butoxy-2-hydroxypropyl, 3-n-amyloxy-2-hydroxypropyl, 3-sec-amyloxy-2-hydroxypropyl, 3-tert-amyloxy-2-hydroxypropyl, 3-isoamyloxy-2-hydroxypropyl, 3-n-hexyloxy-2-hydroxypropyl, 3-cyclohexyloxy-2-hydroxypropyl, 3-n-heptyloxy-2-hydroxypropyl, 3-n-octyloxy-2-hydroxypropyl, 3-(2-ethylhexyl)oxy-2-hydroxypropyl, 3-nonyloxy-2-hydroxypropyl, 3-isononyloxy-2-hydroxypropyl, 3-decyloxy-2-hydroxypropyl, 3-isodecyloxy-2-hydroxypropyl, 3-undecyloxy-2-hydroxypropyl, 3-lauryloxy-2-hydroxypropyl, 3-tridecyloxy-2-hydroxypropyl, 3-isotridecyloxy-2-hydroxypropyl, 3-myristyloxy-2-hydroxypropyl, 3-cetyloxy-2-hydroxypropyl, 3-isocetyloxy-2-hydroxypropyl, 3-stearyloxy-2-hydroxypropyl, 3-isostearyloxy-2-hydroxypropyl, 3-oleyloxy-2-hydroxypropyl, 3-behenyloxy-2-hydroxypropyl and the like groups.

As $R^2$, $R^5$, $R^7$, $R^9$, $R^{11}$, $R^{13}$, $R^{15}$ and $R^{18}$, there may be mentioned hydrogen atom and methyl, ethyl, propyl, isopropyl, n-butyl, isobutyl, sec-butyl, tert-butyl, n-amyl, sec-amyli tert-amyl, isoamyl, n-hexyl, cyclohexyl, n-heptyl, n-octyl, 2-ethylhexyl, nonyl, isononyl, decyl, isodecyl, undecyl, lauryl, tridecyl, isotridecyl, myristyl, cetyl, isocetyl, stearyl, isostearyl, oleyl, behenyl, 2-hydroxyethyl, 2-hydroxypropyl, 2-hydroxyisopropyl, 2-hydroxy-n-butyl, 2-hydroxyisobutyl, 2-hydroxy-sec-butyl, 2-hydroxy-tert-butyl, 2-hydroxy-n-amyl, 2-hydroxy-sec-amyl, 2-hydroxy-tert-amyl, 2-hydroxyisoamyl, 2-hydroxy-n-hexyl, 2-hydroxycyclohexyl, 2-hydroxy-n-heptyl, 2-hydroxy-n-octyl, 2-hydroxy-2-ethylhexyl, 2-hydroxynonyl, 2-hydroxyisononyl, 2-hydroxydecyl, 2-hydroxyisodecyl, 2-hydroxyundecyl, 2-hydroxylauryl, 2-hydroxytridecyl, 2-hydroxyi-sotridecyl, 2-hydroxymyristyl, 2-hydroxycetyl, 2-hydroxyisocetyl, 2-hydroxystearyl, 2-hydroxyisostearyl, 2-hydroxyoleyl, 2-hydroxybehenyl, 2-methoxy-2-hydroxypropyl, 2-ethoxy-2-hydroxypropyl, 3-propoxy-2-hydroxypropyl, 2-isopropoxy-2-hydroxypropyl, 3-n-butoxy-2-hydroxypropyl, 3-isobutoxy-2-hydroxypropyl, 3-sec-butoxy-2-hydroxypropyl, 3-tert-butoxy-2-hydroxypropyl, 3-n-amyloxy-2-hydroxypropyl, 3-sec-amyloxy-2-hydroxypropyl, 3-tert-amyloxy-2-hydroxypropyl, 3-isoamyloxy-2-hydroxypropyl, 3-n-hexyloxy-2-hydroxypropyl, 3-cyclohexyloxy-2-hydroxypropyl, 3-n-heptyloxy-2-hydroxypropyl, 3-n-octyloxy-2-hydroxypropyl, 3-(2-ethylhexyl)oxy-2-hydroxypropyl, 3-nonyloxy-2-hydroxypropyl, 3-isononyloxy-2-hydroxypropyl, 3-decyloxy-2-hydroxypropyl, 3-isodecyloxy-2-hydroxypropyl, 3-undecyloxy-2-hydroxypropyl, 3-lauryloxy-2-hydroxypropyl, 3-tridecyloxy-2-hydroxypropyl, 3-isotridecyloxy-2-hydroxypropyl, 3-myristyloxy-2-hydroxypropyl, 3-cetyloxy-2-hydroxypropyl, 3-3-isocetyloxy-2-hydroxypropyl, 3-stearyloxy-2-hydroxypropyl, 3-isostearyloxy-2-hydroxypropyl, 3-oleyloxy-2-hydroxypropyl, 3-behenyloxy-2-hydroxypropyl and the like groups.

The cysteine or cystine derivatives represented by the above-described general formula (I), (II), (III) or (IV) may be either in the optically active form or racemic form. Among them, L and DL forms are preferred. As the salts of the compound represented by the above-described general formula (I), (II), (III) or (IV), there may be mentioned hydrohalogenides such as hydrochloride, hydrobromide, hydroiodide and the like; salts of an inorganic acid such as sulfate, carbonate, phosphate and the like; and salts of an organic acid such as acetate, tartrate, citrate, p-toluenesulfonate, glycolate, malate, lactate, fatty acid salt, acidic amino acid salts, pyrroglutamate and the like. These salts may be used either singly or in combination.

Next will be made a description of a process for producing the compounds of the present invention.

The cysteine or cystine derivative represented by the above-described general formula (I), (II), (III) or (IV) can be led to its amide or ester from by reacting, for example, L- or DL-cysteine or L- or DL-cystine with an acid anhydride, acid chloride, alkyl halide, epoxy alkane or alkyl glycidyl ether, whereby the amino group is acylated, alkylated, hydroxyalkylated or 3-alkoxy-2-hydroxypropylated, and then subjecting the resulting compound to dehydration-condensation with an alkyl amine or an alcohol.

The cysteine or cystine derivative represented by the above-described general formula (I) or (IV) can be produced, for example, by reacting L- or DL-cysteine amide or L- or DL-cystine diamide with an acid anhydride, acid chloride, alkyl halide, epoxy alkane or alkyl glycidyl ether, whereby the amino group is acylated, alkylated, hydroxyalkylated or 3-alkoxy-2-hydroxypropylated.

The cysteine or cystine derivative represented by the above-described general formula (II), (III) or (IV) can be produced, for example, by reacting L- or DL-cysteine ester or L- or DL-cystine diester with an acid anhydride, acid chloride, alkyl halide, epoxy alkane or alkyl glycidyl ether, whereby the amino group is acylated, alkylated, hydroxyalkylated or 3-alkoxy-2-hydroxypropylated.

In the next place, the above-described Component (B) to be used, in combination with the compound of the present invention, for preparing the cosmetic composition or dermatologic preparation for external use according to the present invention.

As the antioxidant as Component (B), there may be mentioned ascorbic acid, sodium ascorbate, ascorbyl stearate, ascorbyl palmitate, ascorbyl dipalmitate, magnesium ascorbate phosphate, α-tocopherol, β-tocopherol, γ-tocopherol, δ-tocopherol, α-tocotrienol, β-tocotrienol, γ-tocotrienol, δ-tocotrienol, tocopherol acetate, natural vitamin E, tocopherol nicotinate, Trolox, N-acetylcysteine, α-lipoic acid, dehydrolipoic acid, glutathione, uric acid, dihydroxytoluene, butylhydroxyanisole, dibutylhydroxytoluene, erysorbic acid, sodium erysorbate, gallic acid, propyl gallate, tannic acid, catechin, caffeic acid, ferulic acid, protocatechuic acid, oryzanol, quercetin, epigallocatechin gallate, carnosol, sesamol, sesamine, sesamolin, zingerone, Shogaol, capsaicin, vanillyl amide, ellagic acid, bromophenol, flavoglacin, melanoidine, retinol, dehydroretinol, vitamin A oil, retinol acetate, retinol palmitate, retinal, retinoic acid, riboflavin, riboflavin butyrate ester, flavin mononucleotide, flavin adenine dinucleotide, superoxide dismutase, ubiquinol, ubiquinone, catalase, glutathione peroxidase, catalase ferroxidase, metallothionein, ceruloplasmin, transferrin, lactoferrin, albumin, bilirubin, citric acid, tartaric acid, malic acid, phytic acid, histidine, tryptophan, O-phosphono-pyridoxylidene rhodamine, N-(2-hydroxybenzyl)amino acid as described in U.S. Pat. No. 5,594,012, N-(4-pyridoxylmethylene)amino acid and the like.

As the anti-inflammatory drug as Component (B), there may be mentioned glycyrrhetinic acid, glyceryl glycyrrhetinate, stearyl glycyrrhetinate, glycyrrhetinyl stearate, glycyrrhizic acid, methyl glycyrrhizinate, dipotassium glycyrrhizinate, salicylic acid, sodium salicylate, resorcin, guaiazulene, allantoin, lithospermum root extract, shikonin, diphenhydramine hydrochloride, chlorpheniramine maleate, ichthammol, γ-oryzanol, thianthol, sodium copper chlorophyllin, ibuprofen, indomethacin, tranexamic acid, hydrocortisone and the like.

As the ultraviolet absorber as Component (B), there may be mentioned 2-hydroxy-4-methoxybenzophenone (oxybenzone), 2-hydroxy-4-methoxybenzophenone-5-sulfonic acid, sodium 2-hydroxy-4-methoxybenzophenone-5-sulfonate, dihydroxydimethoxybenzophenone, sodium dihydroxydimethoxybenzophenonesulfonate, 2,4-dihydroxybenzophenone, tetrahydroxybenzophenone, p-aminobenzoic acid, sodium p-aminobenzoate, ethyl p-aminobenzoate, glyceryl p-aminobenzoate, amyl p-dimethylaminobenzoate, 2-ethylhexyl p-dimethylaminobenzoate, ethyl p-methoxycinnamate, isopropyl p-methoxycinnamate, 2-ethylhexyl p-methoxycinnamate (cinnoxate), 2-ethoxyethyl p-methoxycinnamate, sodium p-methoxycinnamate, potassium p-methoxycinnamate, glyceryl di(p-methoxycinnamic acid)mono-2-ethylhexanoate, methyl diisopropylcinnamate, 2-ethylhexyl salicylate, phenyl salicylate, homomenthyl salicylate, dipropylene glycol salicylate, ethylene glycol salicylate, myristyl salicylate, methyl salicylate, 4-tertbutyl-4'-methoxydibenzoylmethane, 2-(2'-hydroxy-5'-methylphenyl)benzotriazole, methyl anthranilate, ethyl anthranilate, urocanic acid, ethyl urbcanate, 2,4,6-tris[4-(2-ethylhexyloxycarbonyl)anilino]-1,3,5-triazine, titanium oxide, 3,3'-(1,4-phenylenedimethylidene)bis(7,7-dimethyl-2-oxo-bicyclo[2.2.1]heptane-1-methanesulfonic acid) (Mexoryl SX), and the like.

Next will be made a description of the way of administering the oxidative stress inhibitor of the present invention.

The oxidative stress inhibitor of the present invention represented by the above-described general formula (I) or (II) can be administered orally or parenterally, but direct administration to an oxidative stress activating system is preferred. Usually, preferred is the use thereof in the form where it is incorporated in a cosmetic composition or dermatologic preparation for external use. In the method of the present invention for preventing, retarding, alleviating or treating a dermal change induced by an oxidative stress or wrinkles or flabbiness of the skin induced by light, preferred is direct administration of a cosmetic composition or dermatologic preparation for external use containing the compound of the above-described general formula (III) to the healthy skin or to any site wherein a dermal change or formation of wrinkles or flabbiness has advanced or is advancing.

When the compound represented by the above-described general formula (I), (II) or (III), or the above-described Components (A) and (B) are incorporated in a cosmetic composition as an effective ingredient for prevention or alleviation of skin injuries caused by an oxidative stress, it can be added in an amount of 0.01 to 10 wt. %, preferably 0.1 to 5 wt. %. When the compound represented by the above-described general formula (I), (II) or (III) or the above-described Components (A) and (B) are incorporated in a dermatologic preparation for external use as an effective ingredient for prevention or treatment of diseases induced from an oxidative stress, it can be added in an amount of 0.01 to 50 wt. %, preferably 0.1 to 20 wt. %. When the amount is less than 0.01 wt. %, the resulting preparation cannot fully exhibit oxidative stress inhibiting function, while when the amount exceeds 50 wt. %, on the other hand, it involves problems in feeling upon use such as creaky feeling onto the skin, and the like. Therefore, amounts outside the above range are not preferred.

It is preferred to continuously apply, to the skin, the cosmetic composition or dermatologic preparation for external use containing the compound represented by the above-described general formula (I), (II) or (III) or the above-described Components (A) and (B) for a long period of time, more specifically, for at least one month. It is more preferred that for the prevention of skin injuries or rag diseases caused by an oxidative stress, the preparation is continuously applied for a period not less than 3 months to the death of the patient, while for the alleviation or treatment of the skin injuries or diseases caused by an oxidative stress, it is applied for a period not less than 3 months to 10 years.

Application frequency preferably ranges from once/week to 5 times/day, with once/day to three times/day being more preferred. The amount of the compound represented by the above-described general formula (I), (II) or (III), or the above-described Components (A) and (B) to be applied preferably ranges from 0.003 $\mu g/cm^2$ to 200 $mg/cm^2$, with 1 $\mu g/cm^2$ to 50 $mg/cm^2$ being more preferred.

When the compound represented by the above-described general formula (I), (II) or (III), or the above-described Components (A) and (B) are incorporated in a cosmetic composition or a dermatologic preparation for external use, components ordinarily employed for a cosmetic composition or dermatologic preparation for external use can be, in addition to the oxidative stress inhibitor of the present invention, added within an extent not damaging the advantages of the present invention.

As such components ordinarily employed for a cosmetic composition or a dermatologic preparation for external use, there may be mentioned oily raw materials, surfactants, solvents, humectants, high-molecular weight substances, powdery substances, colorants, perfumes, percutaneous absorption promoters, components derived from animals or plants, and the like.

As the oily raw material, there may be mentioned oils and fats such as animal and vegetable oils, waxes such as lanolin, hydrocarbons such as paraffin, higher alcohols such as cetanol, higher fatty acids such as stearic acid, sterols, phospholipids such as lecithin, synthetic esters such as myristic acid, metal soaps, silicone oils and the like.

As the surfactant, there may be mentioned anionic surfactants, cationic surfactants, amphoteric surfactants, nonionic surfactants, emulsifiers, solubilizing agents, and the like.

As the solvent, there may be mentioned lower alcohols such as ethanol, ethers, glycerins, liquid nonionic surfactants, liquid oily raw materials, other organic solvents, water, and the like.

As the humectant, there may be mentioned polyhydric alcohols such as glycerin, salts of an organic acid such as pyrrolidonecarboxylic acid, urea, mucopolysaccharides such as hyaluronic acid, salts of an amino acid such as proline, and the like.

As the high molecular weight substance, there may be mentioned natural high molecular weight compounds such as collagen, semi-synthetic high molecular weight compounds such as partially deacetylated chitin, synthetic high molecular weight compounds such as carboxymethyl cellulose, and the like.

As the powdery substance, there may be mentioned inorganic pigments such as talc, functional pigments such as synthetic mica, hybrid fine powder, pearl-lustrous pigments such as titanium-dioxide coated mica, photochromic pigments, high molecular powders such as nylon powder, organic powders such as $N^\epsilon$-lauroyl lysine, and the like.

As the colorant, there may be mentioned legal 1st-class tar pigments, legal 2nd-class tar pigments, legal 3rd-class tar pigments, hair dyes, natural colorants, mineral colorants, and the like.

As the perfume, there may be mentioned animal perfumes such as musk, plant perfumes such as jasmine oil, synthetic perfumes such as α-amylcinnamaldehyde, mixed perfumes, and the like.

As percutaneous absorption promoters, there may be mentioned urea, 2-pyrrolidone, 1-hexanol, 1-octanol, 1-decanol, 1-menthol, sodium lauryl sulfate, isopropyl myristate, n-hexyl acetate, oleic acid, and the like.

As the components derived from animals or plants, there may be mentioned licorice extract, placenta extract, aqueous hamamelis, and the like.

No particular limitations are imposed on the dosage form of the cosmetic composition or dermatologic preparation for external use containing the above-described general formula (I), (II) or (III) or the above-described Components (A) and (B), and any dosage form such as solution, paste, gel, solid or powder can be adopted. The cosmetic composition or dermatologic preparation for external use according to the present invention can be used as or for oil, lotion, cream, milky lotion, gel, shampoo, hair rinse, hair conditioner, enamel, foundation, lipstick, face powder, pack, ointment, tablet, injection, granule, capsule, perfume, powder, eau de Cologne, dental paste, soap, aerosol, cleansing foam and the like; and also as or for skin aging preventive or alleviative, skin inflammation preventive or alleviative, bath agent, hair tonic, skin vitalizing lotion, sunburn preventive, preventive or alleviative of photosensitivity such as xeroderma pigmentosum or solar urticaria, preventive or alleviative of photoallergy, preventive or alleviative of optical immunosuppression, preventive or alleviative of rough skin caused by injury, chaps, cleft or the like, and the like. It can be used as or for a preventive and/or curative for various diseases induced by the activation of an oxidative stress, e.g., rheumatic diseases such as rheumatoid arthritis and the like, arthritis, skin diseases such as atopic dermatitis, contact dermatitis, psoriasis vulgaris and the like, respiratory diseases such as bronchial asthma, bronchitis and the like, inflammatory bowel diseases, acute or chronic hepatitis, acute or chronic nephritis, Mediterranean fever, ischemic diseases such as myocardial infarction, and the like.

To the cosmetic composition or dermatologic preparation for external use containing the compound represented by the above-described general formula (I), (II) or (III) or the above-described Components (A) and (B), other ordinarily employed components in cosmetic compositions or dermatologic preparations for external use a can be added within an extent not impairing the advantages of the present invention. As such other ordinarily employed components in cosmetic compositions or dermatologic preparations for external use, there may be mentioned antiseptic bactericides, antioxidants, chelating agents, discoloration preventives, buffers, medicaments for acne vulgaris, antidandruffs or antipruritics, antiperspirants or antibromics, antipyrotics, acaricides or pediculicides, keratin softeners, medicaments for xeroderma, virucides, hormones, vitamins, amino acids, peptides, proteins, astringents, coolants, melanin synthesis inhibitors (whitening agents), antibiotics, antimycotics, hair growth promoters and the like.

Best Mode for Carrying out the Invention

The present invention will be hereinafter described in greater detail with reference to Examples (Synthesis Examples, Test Examples and Formulation Examples). It should however be borne in mind that the present invention is not limited to or by these Examples. In these Examples, the amount of each component is indicated by wt. %.

First, Synthesis Examples will be described.

SYNTHESIS EXAMPLE 1

Synthesis of Cystine Diamide Derivatives

To 7 ml of acetonitrile were added successively 0.15 g of L-cystine diamide dihydrochloride, 0.21 g of n-hexanoic anhydride and 0.10 g of triethylamine, followed by stirring overnight at room temperature. The reaction mixture was concentrated, and the crude crystals thus obtained were purified by high-performance liquid chromatography (HPLC separation with an apparatus for high-performance liquid chromatography manufactured by Hitachi, Ltd. wherein "Inertsil ODS-3 Column" (ex GL Science) is used), whereby 0.18 g of N,N'-di(n-hexanoyl)-L-cystine diamide was obtained.

Similarly, various N,N'-diacyl-L-cystine diamides were obtained. They are novel compounds not yet published. The measuring results of mass spectra of these compounds are shown in Table 1.

TABLE 1

| New Compounds | Mass Spectra (M + H) | |
|---|---|---|
| | Measured | Calcd. |
| N,N'-di(butyryl)-L-cystine diamide | 379 | 379 |
| N,N'-di(n-valeryl)-L-cystine diamide | 407 | 407 |
| N,N'-di(n-hexanoyl)-L-cystine diamide | 435 | 435 |
| N,N'-di(octanoyl)-L-cystine diamide | 491 | 491 |

SYNTHESIS EXAMPLE 2

Synthesis of Cystine Dialkyl Ester Derivatives

To 25 ml of acetonitrile were added successively 0.50 g of L-cystine dimethyl ester dihydrochloride, 0.55 g of n-pentanoic anhydride and 0.31 g of triethylamine, followed by stirring overnight at room temperature. The reaction mixture was concentrated, and the crude crystals thus obtained were purified by high-performance liquid chromatography as in Synthesis Example 1, whereby 0.38 g of N,N'-di(n-valeryl)-L-cystine dimethyl ester was obtained.

Similarly, various N,N'-diacyl-L-cystine dialkyl esters and N,N'-diacyl-DL-homocystine dialkyl esters were obtained.

Next will be given Test Examples.

TEST EXAMPLE 1

Test on the Function of Inhibiting the Activation of NF-κB Induced by Ultraviolet Rays Each of the test compounds was added to a culture plate at a concentration within an extent not causing a damage to the human epidermal cells which had reached the confluent stage in the culture plate. After 18 hours had elapsed, the culture medium was substituted by a phenol red-free medium. The cells were exposed to ultraviolet rays (UVB: 50 mJ/cm$^2$) from an ultraviolet irradiator "Dermaray M-DMR-80" (ex Toshiba Medical Supply Co., Ltd.). After 4 to 5 hours had elapsed, the cells were collected, and the nucleoprotein was extracted therefrom in a manner known per se in the art. From the resulting nucleoprotein, the activated NF-κB was detected in accordance with the gel shift assay. The amount of the NF-κB was determined by measuring the radioactive value of the NF-κB band with the use of a bioimaging analyzer "BAS 2000" (ex Fuji Film Co., Ltd.).

The inhibition ratio of the activation of the NF-κB of the test compounds was calculated from the below-described formula (1). The results of the test compounds of the present invention are shown below in Table 2a, while those of the comparative compounds are shown below in Table 2b.

Inhibition ratio of NF-κB activation (%)

$$=\{1-(A_1-A_3)/(A_2-A_3)\}\times 100 \quad (1)$$

wherein, A1: radioactive value of the NF-κB upon addition of a test compound

A2: radioactive value of NF-κB when a test compound is not added

A3: radioactive value of NF-κB when a test compound is not added and is not exposed to ultraviolet rays.

TABLE 2a

| Test compounds | Addition concentration (mM) | Inhibition ratio (%) |
|---|---|---|
| N,N'-di (n-butyryl)-L-cystine diamide | 0.01 | 45 |
| | 0.1 | 11 |
| N,N'-di (n-valeryl)-L-cystine diamide | 0.01 | 8 |
| | 0.1 | 53 |
| N,N'-di (n-hexanoyl)-L-cystine diamide | 0.01 | 24 |
| | 0.1 | 93 |
| N,N'-di (n-octanoyl)-L-cystine diamide | 0.01 | 66 |
| | 0.1 | 61 |
| N,N'-diacetyl-L-cystine dimethyl ester | 0.01 | 47 |
| | 0.1 | 86 |
| N,N'-diacetyl-L-cystine diethyl ester | 0.01 | 37 |
| | 0.1 | 107 |
| N,N'-diacetyl-L-cystine diisopropyl ester | 0.01 | 19 |
| | 0.1 | 48 |
| N,N'-di (n-propionyl)-L-cystine dimethyl ester | 0.01 | 17 |
| | 0.1 | 54 |
| N,N'-di (n-butyryl)-L-cystine dimethyl ester | 0.01 | 52 |
| | 0.1 | 79 |
| N,N'-di (n-valeryl)-L-cystine dimethyl ester | 0.01 | 18 |
| | 0.1 | 64 |
| N,N'-di (n-hexanoyl)-L-cystine dimethyl ester | 0.01 | 43 |
| | 0.1 | 77 |
| N,N'-di (n-heptanoyl)-L-cystine dimethyl ester | 0.01 | 25 |
| | 0.1 | 103 |
| N,N'-di (n-octanoyl)-L-cystine dimethyl ester | 0.01 | 33 |
| | 0.1 | 91 |
| N,N'-di (n-decanoyl)-L-cystine dimethyl ester | 0.01 | 56 |
| | 0.1 | 68 |
| N,N'-dilauroyl-L-cystine dimethyl ester | 0.01 | 52 |
| | 0.1 | 59 |
| N,N'-diacetyl-DL-homocystine dimethyl ester | 0.01 | 10 |
| | 0.1 | 46 |
| L-cysteine ethyl ester | 0.5 | 60 |
| | 1 | 61 |
| | 5 | Toxicity expressed |
| N-acetyl-L-cysteine methyl ester | 0.01 | 28 |
| | 0.1 | 95 |
| N-acetyl-L-cysteine ethyl ester | 0.01 | 31 |
| | 0.1 | 74 |
| N-acetyl-L-cystine isopropylester | 0.01 | 21 |
| | 0.1 | 82 |
| N,S-diacetyl-L-cystine methyl ester | 0.01 | 20 |
| | 0.1 | 31 |
| L-cystine diethyl ester | 0.1 | 50 |
| | 0.5 | >100 |
| | 1 | Toxicity expressed |
| N-lauroyl-L-cysteine | 0.1 | 14 |
| | 0.5 | 86 |
| | 10 | Toxicity expressed |
| N-lauroyl-L-cysteine methyl ester | 0.01 | 36 |
| | 0.1 | 43 |

TABLE 2b

| Test compounds | Addition concentration (mM) | Inhibition ratio (%) |
|---|---|---|
| desferrioxamine | 1 | −83 |
| | 5 | −112 |
| | 10 | Toxicity expressed |
| pyrrolidine dithiocarbamate | 0.005 | −2 |
| | 0.01 | 9 |
| | 0.05 | Toxicity expressed |
| N-acetyl-L-cysteine | 10 | 23 |
| | 30 | 55 |
| | 50 | Toxicity expressed |

TABLE 2b-continued

| Test compounds | Addition concentration (mM) | Inhibition ratio (%) |
|---|---|---|
| N,N'-diacetyl-L-cystine | 10 | 48 |
| | 30 | 67 |
| | 50 | Toxicity expressed |

As shown in Table 2b, known NF-κB activation inhibitors such as desferrioxamine (ex. AIDS Reseasrch and Human Retroviruses, Vol. 11, pp. 1049 to 1061, 1995) or pyrrolidines dithiocarbamate (ex. Immunology, Vol. 90, pp. 445–460, 1997) did not exhibit the NF-κB activation inhibiting function in this test, while as shown in Table 2a, any compounds according to the present invention exhibited the suppressing or inhibiting function. In addition, the compounds according to the present invention exhibited their suppressing activity at a concentration not greater than 0.5 mM, higher than of N-acetyl-L-cysteine or N,N'-diacetyl-L-cystine (as shown in Table 2b) which exhibited their inhibiting function only at a concentration not less than 1 mM. From these results, it can be understood that the compounds according to the present invention has high oxidative stress suppressing or inhibiting function.

TEST EXAMPLE 2

Test on Suppressing Function of Wrinkles Formation Induced by Ultraviolet Rays (No. 1)

Hairless mice (SKH-1, female, 5–6 weeks old) were exposed to ultraviolet rays (UVB) three times/week (Monday, Wednesday and Friday) for 5 weeks, each at 50 to 100 mJ/cm$^2$ by using the above-described "Dermaray M-DMR-80" (ex Toshiba Medical Supply Co., Ltd.). The test compound (N,N'-diacetyl-L-cystine dimethyl ester) was dissolved in a mixed solvent of propylene glycol, ethanol and water, and was applied to the back portion of each of the mice in an amount of 100 μl, 30 to 60 minutes before exposure to ultraviolet rays, just after the completion of the exposure, and on the days free from exposure to ultraviolet rays (Sunday, Tuesday, Thursday and Saturday). From two weeks after the exposure had started, the wrinkles formed on the back portion of each mouse were evaluated once a week based on the below-described standards, and they were indicated as scores. In addition, the function of the inventive compound for inhibiting wrinkle formation induced by ultraviolet rays was judged based on the below-described judging standards. The results are shown below in Table 3.

| | | Evaluation standards |
|---|---|---|
| Score: | 0 | Formation of wrinkles is not recognized. |
| Score: | 1 | Anisotropic formation of fine wrinkles is recognized. |
| Score: | 2 | Isotropic formation of fine wrinkles is recognized. |
| Score: | 3 | Wrinkles of Score 2 but having increased depth are recognized. |
| Score: | 4 | Formation of evident and deep wrinkles is recognized. |
| Score: | 5 | Formation of evident and deep wrinkles with flabbiness is recognized. |

-continued

Judging standards

| | | |
|---|---|---|
| Judgment: | ⊚ | The average score of the inventive product-applied group is lower by at least 1.5 than that of the solvent-applied group. |
| Judgment: | ○ | Lower by at least 1.0 but less than 1.5 in the same comparison. |
| Judgment: | Δ | lower by at least 0.5 but less than 1.0 in the same comparison. |
| Judgment: | X | lower by less than 0.5 in the same comparison. |

TABLE 3

| | | Score and judgment | | | |
|---|---|---|---|---|---|
| Groups | Mouse No. | 2nd week | 3rd week | 4th week | 5th week |
| Solvent-applied group | 1 | 3 | 3 | 3 | 3 |
| | 2 | 3 | 4 | 4 | 4 |
| | 3 | 3 | 4 | 4 | 5 |
| | 4 | 3 | 4 | 4 | 5 |
| | 5 | 1 | 4 | 4 | 5 |
| | 6 | 2 | 2 | 4 | 4 |
| | 7 | 3 | 4 | 5 | 5 |
| | Average | 2.6 | 3.6 | 4.0 | 4.4 |
| 10% N,N'-diacetyl-L-cystine dimethyl ester-applied group | 8 | 2 | 2 | 3 | 2 |
| | 9 | 1 | 3 | 5 | 3 |
| | 10 | 1 | 1 | 5 | 4 |
| | 11 | 0 | 2 | 2 | 2 |
| | 12 | 1 | 2 | 3 | 2 |
| | 13 | 3 | 2 | 3 | 3 |
| | 14 | 1 | 2 | 4 | 3 |
| | Average | 1.3 | 2.0 | 3.6 | 2.7 |
| | Judgment | ○ | ⊚ | Δ | ○ |

As shown in Table 3, N,N'-diacetyl-L-cystine dimethyl ester exhibited effects for retarding and alleviating the wrinkle formation induced by ultraviolet rays, suggesting that the compounds of the present invention are useful as an effective ingredient in a method for preventing, retarding, alleviating or treating a dermal change induced by an oxidative stress.

TEST EXAMPLE 3

Test on the Function of Inhibiting the AP-1 Activation Induced by Ultraviolet Rays In a similar manner to Test Example 1, a nucleoprotein was obtained. Then, the activated AP-1 was detected by the gel shift assay. The radioactive value of the AP-1 band was measured as in Test Example 1, whereby the amount of the AP-1 was determined. The AP-1 activation inhibiting ratio of the test compounds was calculated by the below-described equation (2). The results of the test compounds according to the present invention are shown below in Table 4a, while those of the comparative compounds are shown below in Table 4b.

AP-1 activation inhibiting ratio (%)

$$=\{1-(B_1-B_3)/(B_2-B_3)\}\times 100 \quad (2)$$

wherein, $B_1$: radioactive value of the AP-1 band upon addition of a test compound.

$B_2$: radioactive value of the AP-1 band when a test compound is not added.

$B_3$: radioactive value of the AP-1 band when a test compound is not added and is not exposed to ultraviolet rays.

TABLE 4a

| Test compounds (Concentration) | Inhibiting ratio (%) |
|---|---|
| N,N'-diacetyl-L-cystine dimethyl ester (10 μM) | 4 |
| dl-α-tocopherol (10 μM) | 5 |
| dl-α-tocopherol (100 μM) | −1 |
| dl-α-tocopherol (10 μM) + N,N'-diacetyl-L-cystine dimethyl ester (10 μM) | 102 |
| L(+)ascorbic acid (0.1 mM) | 1 |
| L(+)ascorbic acid (1 mM) | 0 |
| L(+)ascorbic acid (1 mM) + N,N'-diacetyl-L-cystine dimethyl ester (10 μM) | 54 |
| N-acetyl-L-cysteine (0.1 mM) | 0 |
| N-acetyl-L-cysteine (1 mM) | −13 |
| N-acetyl-L-cysteine (1 mM) + N,N'-diacetyl-L-cystine dimethyl ester (10 μM) | 53 |
| glycyrrhetinic acid (10 μM) | 2 |
| glycyrrhetinic acid (100 μM) | −104 |
| glycyrrhetinic acid (10 μM) + N,N'-diacetyl-L-cystine dimethyl ester (10 μM) | 85 |
| glycyrrhizic acid (0.1 mM) | −3 |
| glycyrrhizic acid (1 mM) | −70 |
| glycyrrhizic acid (0.1 mM) + N,N'-diacetyl-L-cystine dimethyl ester (10 μM) | 39 |
| 4-tert-butyl-4'-methoxybenzoylmethane (1 μM) | −14 |
| 4-tert-butyl-4'-methoxybenzoylmethane (10 μM) | 17 |
| 4-tert-butyl-4'-methoxybenzoylmethane (1 μM) + N,N'-diacetyl-L-cystine dimethyl ester (10 μM) | 31 |
| 2-ethylhexyl p-methoxycinnamate (10 μM) | −20 |
| 2-ethylhexyl p-methoxycinnamate (100 μM) | 11 |
| 2-ethylhexyl p-methoxycinnamate (10 μM) + | 103 |

TABLE 4b

| Test compounds (Concentration) | Inhibiting ratio (%) |
|---|---|
| astaxantin (1 μM) | −54 |
| astaxantin (10 μM) | 0 |
| astaxantin (100 μM) | Toxicity expressed |
| astaxantin (10 μM) + N,N'-diacetyl-L-cystine dimethyl ester (10 μM) | −16 |

As shown in Tables 4a and 4b, the above-described Components (A) and (B) when combined, exhibited a marked inhibiting function. The inhibiting function in such combination exceeded that of each of Components (A) and (B). This fact suggests that the oxidative stress activation can be inhibited or supressed more by synergism of the effects of Components (A) and (B).

TEST EXAMPLE 4

Test on Inhibiting Function of Wrinkles Formation induced by Ultraviolet Rays (No. 2)

Function of suppressing ultraviolet ray-induced wrinkles formation by the synergistic effects when Components (A) and (B) were used in combination, was judged in a similar manner to Test Example 2. Fifteen to twenty mice were divided into 4 groups, that is, a 1st group to which a mixed solvent of propylene glycol, ethanol and water was to be applied, a 2nd group to which a solution of only Component (A) dissolved in the above-described solvent was to be applied, a 3rd group to which a solution of only Component (B) dissolved in the above-described solvent was to be applied, and a 4th group to which a solution of both Components (A) and (B) dissolved in the above-described solvent was to be applied. An average score of each group was determined. The results are shown below in Table 5.

TABLE 5

| Text compounds (Concentration) | Score | | | |
|---|---|---|---|---|
| | 2nd week | 3rd week | 4th week | 5th week |
| Solvent | 3.0 | 3.7 | 4.7 | 3.7 |
| N,N'-diacetyl-L-cystine dimethyl ester (10%) | 1.5 | 2.5 | 3.0 | 4.0 |
| dl-α-tocopherol (5%) | 2.0 | 3.0 | 2.5 | 3.5 |
| dl-α-tocopherol (5%) + N,N'-diacetyl-L-cystine dimethyl ester (10%) | 2.0 | 3.0 | 2.0 | 2.7 |
| Solvent | 2.3 | 4.0 | 4.3 | 4.7 |
| N,N'-diacetyl-L-cystine dimethyl ester (10%) | 1.0 | 1.0 | 5.0 | 4.0 |
| L(+)-ascorbic acid (5%) | 1.0 | 2.0 | 4.0 | 4.0 |
| L(+)-ascorbic acid (5%) + N,N'-diacetyl-L-cystine dimethyl ester (10%) | 1.0 | 1.3 | 2.3 | 3.3 |
| Solvent | 3.0 | 3.7 | 4.7 | 3.7 |
| N,N'-diacetyl-L-cystine dimethyl ester (10%) | 1.5 | 2.5 | 3.0 | 4.0 |
| Salicylic acid (5%) | 2.0 | 1.5 | 1.5 | 2.5 |
| Salicylic acid (5%) + N,N'-diacetyl-L-cystine dimethyl ester (10%) | 1.0 | 1.0 | 1.7 | 2.7 |
| Solvent | 1.3 | 1.7 | 3.3 | 3.0 |
| N,N'-diacetyl-L-cystine dimethyl ester (10%) | 0.5 | 2.0 | 2.5 | 2.0 |
| 2-ethylhexyl p-methoxycinnmate (3%) | 0.0 | 0.5 | 1.5 | 0.5 |
| 2-ethylhexyl p-methoxycinnmate (3%) + N,N'-diacetyl-L-cystine dimethyl ester (10%) | 0.0 | 0.7 | 0.3 | 0.0 |

As shown in Table 5, the inhibiting function of the Components (A) and (B) when used in combination, exceeded that of Component (A) or (B) when used each singly. For example, N,N'-diacetyl-L-cystine dimethyl ester when used in combination with dl-α-tocopherol, ascorbic acid, or 2-ethyl p-methoxycinnamate, gave synergistic effects from four weeks after the ultraviolet exposure had started. And, N,N'-diacetyl-L-cystine dimethyl ester when used in combination with salicylic acid gave synergistic effects from Week 2 or Week 3. According to the present invention, a dermal change caused by an oxidative stress can be suppressed by synergism of Components (A) and (B) when used in combination.

Finally, Formulation Examples 1–13 of various preparations will be given, using an oxidative stress inhibitor of the present invention.

Formulation Example 1: Tablet

| N-acetyl-L-laurylamide | 5% |
|---|---|
| N,N'-dilauroyl-L-cystine dimethyl ester | 5 |
| Lactose | 50 |
| Starch | 20 |
| Carboxymethyl cellulose | 19 |
| Magnesium stearate | 1 |

Formulation Example 2: Injection

| N-lauroyl-L-cysteine amide | 0.1% |
|---|---|
| Glucose | 2.0 |
| Distilled water for injection | Balance |

Formulation Example 3: Ointment

| L-Cysteine lauryl amide | 0.5% |
|---|---|
| N-lauroyl-L-cysteine | 1.0 |
| Urea | 20.0 |
| White vaseline | 15.0 |
| Light liquid paraffin | 6.0 |
| Cetanol | 3.0 |
| Stearyl alcohol | 3.0 |
| Glyceryl monostearate | 5.0 |
| Perfume | q.s. |
| Antiseptic | q.s. |
| Buffer | 1.0 |
| Purified water | Balance |

Formulation Example 4: Cream

| N,N'-diacetyl-L-cystine dimethyl ester | 1.0% |
|---|---|
| Magnesium ascorbate phosphate | 1.0 |
| Stearic acid | 2.0 |
| Polyoxyethylene (25) cetyl ether | 3.0 |
| Glyceryl monostearate | 2.0 |
| Octyl dodecanol | 10.0 |
| Cetanol | 6.0 |
| Reduced lanolin | 4.0 |
| Squalane | 9.0 |
| 1,3-Butylene glycol | 6.0 |
| Polyethylene glycol (1500) | 4.0 |
| Antiseptic | q.s. |
| Perfume | q.s. |
| Antioxidant | q.s. |
| Purified water | Balance |

Formulation Example 5: Cream

| N,N'-diacetyl-L-cystine diisopropyl ester | 1.0% |
|---|---|
| N,N'-di(n-butyryl)-L-cystine amide | 1.0 |
| Glyceryl monostearate | 2.0 |
| Polyoxyethylene (20) sorbitan monolaurate | 1.0 |
| Paraffin | 5.0 |
| Bees wax | 10.0 |
| Vaseline | 15.0 |
| Liquid paraffin | 41.0 |
| Boric acid | 0.2 |
| 1,3-Butylene glycol | 4.0 |
| Antiseptic | q.s. |
| Perfume | q.s. |
| Purified water | Balance |

Formulation Example 6: Milky lotion

| L-cysteine ethyl ester | 2.0% |
|---|---|
| N-acetyl-L-cysteine ethyl ester | 1.0 |
| Retinol | 0.1 |
| Bees wax | 0.5 |
| Vaseline | 2.0 |
| Glyceryl monostearate | 1.0 |
| Polyethylene glycol monooleate | 1.0 |
| Methyl polysiloxane | 2.0 |
| Cetanol | 1.0 |
| Squalane | 6.0 |
| Corboxyvinyl polymer | 0.5 |
| 1,3-Butylene glycol | 4.0 |
| Ethanol | 5.0 |
| Antiseptic | q.s. |
| Perfume | q.s. |
| Purified water | Balance |

Formulation Example 7: Milky lotion

| N,N'-di(n-hexanoyl)-L-cystine ester diamide | 1.5% |
|---|---|
| N-lauroyl-L-cysteine methyl ester | 0.5 |
| Sodium salicylate | 0.1 |
| Sorbitan sesquioleate | 1.6 |
| Polyoxyethylene oleyl ether | 2.4 |
| Stearyl alcohol | 0.5 |
| Hardened palm oil | 3.0 |
| Liquid paraffin | 35.0 |
| Dipropylene glycol | 6.0 |
| Polyethylene glycol (400) | 4.0 |
| Corboxyvinyl polymer (aqueous 1% solution) | 15.0 |
| Potassium hydroxide | 0.1 |
| Antiseptic | q.s. |

-continued

| | |
|---|---|
| Perfume | q.s. |
| Purified water | Balance |
| Formulation Example 8: Gel | |
| N-monolauroyl-L-cystine | 0.05% |
| Liquid paraffin | 12.0 |
| Glyceryl tri(2-ethylhexanoate) | 50.0 |
| Sorbitol | 10.0 |
| Polyethylene glycol (400) | 5.0 |
| Acylmethyl taurine | 5.0 |
| Polyoxyethylene (20) isocetyl ether | 10.0 |
| Perfume | q.s. |
| Antiseptic | q.s. |
| Purified water | Balance |
| Formulation Example 9: Vitalizing lotion | |
| N,N'-diacetyl-L-cystine dimethyl ester | 0.5% |
| Dipropylene glycol | 5.0 |
| Polyethylene glycol (400) | 5.0 |
| Ethanol | 10.0 |
| Carboxyvinyl polymer | 0.5 |
| Sodium alginate | 0.5 |
| Potassium hydroxide | 0.2 |
| Polyoxyethylene (20) sorbitan monostearate | 1.0 |
| Sorbitan monooleate | 0.5 |
| Oleyl alcohol | 0.5 |
| Placenta extract | 0.2 |
| dl-α-tocopherol acetate | 0.2 |
| Perfume | q.s. |
| Antiseptic | q.s. |
| Discoloration inhibitor | q.s. |
| Purified water | Balance |
| Formulation Example 10: Vitalizing lotion | |
| N,N'-diacetyl-L-cystine dimethyl ester | 1.5% |
| 2-Ethylhexyl p-methoxycinnamate | 4.0 |
| 3,3'-(1,4-phenylenedimethylidyne) bis (7,7-dimethyl-2-oxo-bicyclo[2.2.1]heptane-1-methanesulfonic acid) | 4.0 |
| Polyoxyethylene cetyl ether | 2.0 |
| Glyceryl monostearate | 2.0 |
| Stearic acid | 3.0 |
| Cetanol | 1.0 |
| Lanolin | 3.0 |
| Liquid paraffin | 5.0 |
| 2-Ethylhexyl stearate | 3.0 |
| 1,3-Butylene glycol | 6.0 |
| Perfume | q.s. |
| Antiseptic | q.s. |
| Purified water | Balance |
| Formulation Example 11: Pack | |
| L-cystine diethyl ester | 3.0% |
| Polyvinyl alcohol | 15.0 |
| Carboxymethyl cellulose | 5.0 |
| 1,3-Butylene glycol | 5.0 |
| Ethanol | 12.0 |
| Polyoxyethylene (20) oleyl ether | 0.5 |
| Perfume | q.s. |
| Antiseptic | q.s. |
| Buffer | q.s. |
| Purified water | Balance |
| Formulation Example 12: Foundation | |
| N-(2-hydroxylauryl)-L-cysteine | 4.0% |
| 4-tert-butyl-4'-methoxybenzoylmethane | 1.0 |
| Liquid paraffin | 10.0 |
| Polyoxyethylene (20) sorbitan Monooleate | 3.5 |
| Propylene glycol | 3.0 |
| Titanium oxide | 9.0 |
| Kaolin | 24.0 |
| Talc | 42.0 |
| Coloring pigment | 3.0 |
| Perfume | q.s. |
| Antiseptic | q.s. |
| Antioxidant | q.s. |
| Formulation Example 13: Face wash | |
| N,S-diacetyl-L-cysteine methyl ester | 1.0% |

-continued

| | |
|---|---|
| Stearyl glycyrrhetinate | 0.1 |
| N-laurylglutamic acid triethanolamine salt | 25.0 |
| Triethanolamine laurate | 5.0 |
| Polyoxyethylene (4) polyoxypropylene (11) butyl ether | 5.0 |
| Licorice extract | 1.0 |
| Ethanol | 3.0 |
| Perfume | q.s. |
| Antiseptic | q.s. |
| Purified water | Balance |

Industrial Applicability

The oxidative stress activation inhibitor or the inhibiting method of the present invention exhibits excellent function, performance or capacity for suppressing or inhibiting the oxidative stress activation. The cosmetic composition or dermatologic preparation for external use containing the oxidative stress inhibitor of the present invention, when applied to the skin, remains on the skin effectively and can not be removed easily, and at the same time provides good feeling upon use.

What is claimed is:

1. A cysteine or cystine compound represented by formula (I) or a salt thereof:

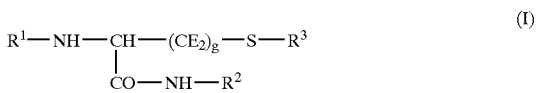

wherein in formula (I):

R$^1$ represents a hydrogen atom; an aminocarbonyl group; an acyl group selected from the group consisting of acetyl, propionyl, isopropionyl, n-butyryl, isobutyryl, sec-butyryl, tert-butyryl, n-valeryl, sec-valeryl, pivaloyl, isovaleryl, n-heptanoyl, nonanoyl, isononanoyl, undecanoyl, tridecanoyl, isotridecanoyl, oleoyl, and docosanoyl; an alkyl group having 1–22 carbon atoms; a hydroxyalkyl group having 1–22 carbon atoms; or a 3-alkoxy-2-hydroxypropyl group whose alkoxyl group has 1–22 carbon atoms;

each E represents, independently, a hydrogen atom or an alkyl group having 1–6 carbon atoms;

g stands for an integer of 0 to 5;

R$^2$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when R$^1$ represents a hydrogen atom or an acyl group having 2–3 carbon atoms, R$^2$ represents an alkyl group having 6–22 carbon atoms, a hydroxyalkyl group having 1–22 carbon atoms or a 3-alkoxy-2-hydroxypropyl group whose alkoxyl group has 1–22 carbon atoms;

R$^3$ represents a hydrogen atom, an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms or a group represented by formula (1):

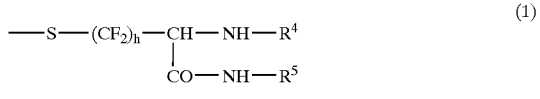

wherein in formula (1):

$R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each F represents, independently, a hydrogen atom or an alkyl group having 1–6 carbon atoms;

h stands for an integer of 0 to 5;

$R^5$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^4$ represents a hydrogen atom or an acyl group having 2–3 carbon atoms, $R^5$ represents an alkyl group having 6–22 carbon atoms, a hydroxyalkyl group having 1–22 carbon atoms or a 3-alkoxy-2-hydroxypropyl group whose alkoxyl group has 1–22 carbon atoms.

2. An oxidative stress inhibitor composition, which comprises, as an effective ingredient, at least one cysteine or cystine compound of formula (I) or salt thereof:

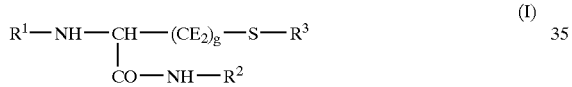

wherein in formula (I):

$R^1$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each E represents, independently, a hydrogen atom or an alkyl group having 1–6 carbon atoms;

g stands for an integer of 0 to 5;

$R^2$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^1$ represents a hydrogen atom or an acyl group having 2–3 carbon atoms, $R^2$ represents an alkyl group having 6–22 carbon atoms, a hydroxyalkyl group having 1–22 carbon atoms or a 3-alkoxy-2-hydroxypropyl group whose alkoxyl group has 1–22 carbon atoms;

$R^3$ represents an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms or a group represented by formula (1):

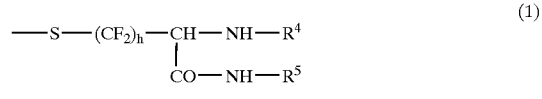

wherein in formula (1):

$R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each F represents, independently, a hydrogen atom or an alkyl group having 1–6 carbon atoms;

h stands for an integer of 0 to 5;

$R^5$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^4$ represents a hydrogen atom or an acyl group having 2–3 carbon atoms, $R^5$ represents an alkyl group having 6–22 carbon atoms, a hydroxyalkyl group having 1–22 carbon atoms or a 3-alkoxy-2-hydroxypropyl group whose alkoxyl group has 1–22 carbon atoms.

3. A method for preventing and/or treating an oxidative stress-induced disease, which comprises treating a subject in need thereof with an effective amount of an oxidative stress inhibitor composition according to claim 1.

4. The method of claim 3, wherein said oxidative stress-induced disease is an ultraviolet rays-induced disease.

5. A cosmetic composition or a dermatologic preparation for external use which comprises:

Component (A) which is at least one cysteine or cystine compound represented by formula (I) or a salt thereof:

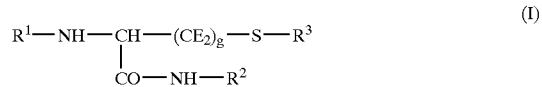

wherein in formula (I):

$R^1$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each E represents, independently, a hydrogen atom or an alkyl group having 1–6 carbon atoms;

g stands for an integer of 0 to 5;

$R^2$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^1$ represents a hydrogen atom or an acyl group having 2–3 carbon atoms, $R^2$ represents an alkyl group having 6–22 carbon atoms, a hydroxyalkyl group having 1–22 carbon atoms or a 3-alkoxy-2-hydroxypropyl group whose alkoxyl group has 1–22 carbon atoms;

$R^3$ represents an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms or a group represented by formula (1):

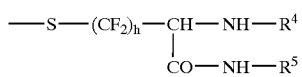
(1)

wherein in formula (1):
$R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each F represents, independently, a hydrogen atom or an alkyl group having 1–6 carbon atoms;

h stands for an integer of 0 to 5;

$R^5$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^4$ represents a hydrogen atom or an acyl group having 2–3 carbon atoms, $R^5$ represents an alkyl group having 6–22 carbon atoms, a hydroxyalkyl group having 1–22 carbon atoms or a 3-alkoxy-2-hydroxypropyl group whose alkoxyl group has 1–22 carbon atoms; and Component (B) which is at least one ingredient selected from the group consisting of antioxidants, anti-inflammatory drugs, and ultraviolet absorbors.

6. The cosmetic composition or dermatologic preparation for external use of claim 5, wherein said anti-oxidant is selected from the group consisting of vitamin C, vitamin E, derivatives thereof, and salts thereof, and N-acetyl cysteine.

7. The cosmetic composition or dermatologic preparation for external use of claim 5, wherein said anti-inflammatory drug is selected from the group consisting of glycyrrhetinic acid, glycyrrhizic acid, or salicylic acid, derivatives thereof, and salts thereof.

8. The cosmetic composition or dermatologic preparation for external use of claim 5, wherein said ultraviolet absorber is selected from the group consisting of benzophenone derivatives, p-aminobenzoic acid and derivatives thereof, methoxycinnamic acid derivatives, salicylic acid derivatives, urocanic acid and derivatives thereof, 4-tert-butyl-4'-methoxy dibenzoylmethane, and 2-(2'-hydroxy-5'-methylphenyl)benzotriazole.

9. The cosmetic composition or dermatologic preparation for external use of claim 5, wherein said at least one cysteine or cystine compound represented by formula (I) or salt thereof is present in an amount of 0.01 to 10 wt. %, based on the weight of said cosmetic composition or dermatologic preparation for external use.

10. The cosmetic composition or dermatologic preparation for external use of claim 5, wherein said at least one cysteine or cystine compound represented by formula (I) or salt thereof is present in an amount of 0.1 to 5 wt. %, based on the weight of said cosmetic composition or dermatologic preparation for external use.

11. The cosmetic composition or dermatologic preparation for external use of claim 5, wherein said at least one cysteine or cystine compound represented by formula (I) or salt thereof is present in an amount of 0.01 to 50 wt. %, based on the weight of said cosmetic composition or dermatologic preparation for external use.

12. The cosmetic composition or dermatologic preparation for external use of claim 5, wherein said at least one cysteine or cystine compound represented by formula (I) or salt thereof is present in an amount of 0.1 to 20 wt. %, based on the weight of said cosmetic composition or dermatologic preparation for external use.

13. A method for preventing, retarding, alleviating or treating a skin change due to aging or an undesirable aesthetic skin change, both caused or promoted by an oxidative stress, which method comprises applying onto the skin a cosmetic composition or a dermatologic preparation for external use which comprises:

Component (A) which is at least one cysteine or cystine compound represented by formula (I) or a salt thereof:

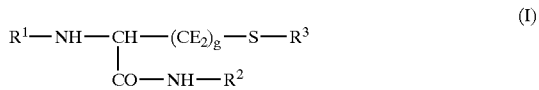
(I)

wherein in formula (I):
$R^1$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each E represents, independently, a hydrogen atom or an alkyl group having 1–6 carbon atoms;

g stands for an integer of 0 to 5;

$R^2$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^1$ represents a hydrogen atom or an acyl group having 2–3 carbon atoms, $R^2$ represents an alkyl group having 6–22 carbon atoms, a hydroxyalkyl group having 1–22 carbon atoms or a 3-alkoxy-2-hydroxypropyl group whose alkoxyl group has 1–22 carbon atoms;

$R^3$ represents a hydrogen atom, an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms or a group represented by formula (1):

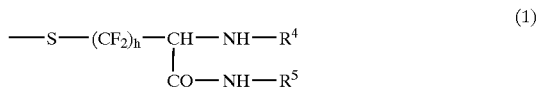
(1)

wherein in formula (1):
$R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each F represents, independently, a hydrogen atom or an alkyl group having 1–6 carbon atoms;

h stands for an integer of 0 to 5;

$R^5$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^4$ represents a hydrogen atom or an acyl group having 2–3 carbon atoms, $R^5$ represents an alkyl group having 6–22 carbon atoms, a hydroxyalkyl group having 1–22 carbon atoms or a 3-alkoxy-2-hydroxypropyl group whose alkoxyl group has 1–22 carbon atoms; and Component (B) which is at least one ingredient selected from the group consisting of antioxidants, anti-inflammatory drugs, and ultraviolet absorbors.

14. The method of claim 13, wherein said skin change due to aging or an undesirable aesthetic skin change, both caused or promoted by an oxidative stress, is induced by sunlight or ultraviolet rays therefrom.

15. The method of claim 13, wherein said anti-oxidant is selected from the group consisting of vitamin C, vitamin E, derivatives thereof, and salts thereof, and N-acetyl cysteine.

16. The method of claim 13, wherein said anti-inflammatory drug is selected from the group consisting of glycyrrhetinic acid, glycyrrhizic acid, or salicylic acid, derivatives thereof, and salts thereof.

17. The method of claim 13, wherein said ultraviolet absorber is selected from the group consisting of benzophenone derivatives, p-aminobenzoic acid and derivatives thereof, methoxycinnamic acid derivatives, salicylic acid derivatives, urocanic acid and derivatives thereof, 4-tert-butyl-4'-methoxy dibenzoylmethane, and 2-(2'-hydroxy-5'-methylphenyl)benzotriazole.

18. The method of claim 13, wherein said at least one cysteine or cystine compound represented by formula (I) or salt thereof is present in an amount of 0.01 to 10 wt. %, based on the weight of said cosmetic composition or dermatologic preparation for external use.

19. The method of claim 13, wherein said at least one cysteine or cystine compound represented by formula (I) or salt thereof is present in an amount of 0.01 to 50 wt. %, based on the weight of said cosmetic composition or dermatologic preparation for external use.

20. The method of claim 13, wherein said at least one cysteine or cystine compound represented by formula (I) or salt thereof is applied to the skin in an amount of 0.003 μg/cm² to 200 mg/cm².

21. A method for treating a skin change due to oxidative stress, which comprises treating a subject in need thereof with an effective amount of an oxidative stress inhibitor composition according to claim 2.

22. The method of claim 21, wherein said skin change is due to an ultraviolet rays-induced disease.

23. A cysteine or cystine compound represented by formula (I) or a salt thereof:

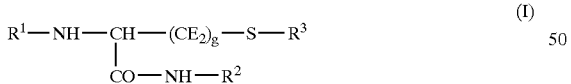

wherein in formula (I):

R¹ represents a hydrogen atom; an aminocarbonyl group; an acyl group selected from the group consisting of acetyl, propionyl, isopropionyl, n-butyryl, isobutyryl, sec-butyryl, tert-butyryl, n-valeryl, sec-valeryl, pivaloyl, isovaleryl, n-heptanoyl, nonanoyl, isononanoyl, undecanoyl, tridecanoyl, isotridecanoyl, and docosanoyl; an alkyl group having 1–22 carbon atoms; a hydroxyalkyl group having 1–22 carbon atoms; or a 3-alkoxy-2-hydroxypropyl group whose alkoxyl group has 1–22 carbon atoms;

each E represents, independently, a hydrogen atom or an alkyl group having 1–6 carbon atoms;

g stands for an integer of 0 to 5;

R² represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when R¹ represents a hydrogen atom or an acyl group having 2–3 carbon atoms, R² represents an alkyl group having 6–22 carbon atoms, a hydroxyalkyl group having 1–22 carbon atoms or a 3-alkoxy-2-hydroxypropyl group whose alkoxyl group has 1–22 carbon atoms;

R³ represents a hydrogen atom, an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms or a group represented by formula (1):

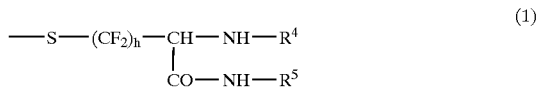

wherein in formula (1):

R⁴ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each F represents, independently, a hydrogen atom or an alkyl group having 1–6 carbon atoms;

h stands for an integer of 0 to 5;

R⁵ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when R⁴ represents a hydrogen atom or an acyl group having 2–3 carbon atoms, R⁵ represents an alkyl group having 6–22 carbon atoms, a hydroxyalkyl group having 1–22 carbon atoms or a 3-alkoxy-2-hydroxypropyl group whose alkoxyl group has 1–22 carbon atoms.

24. A cysteine or cystine compound represented by formula (I) or a salt thereof:

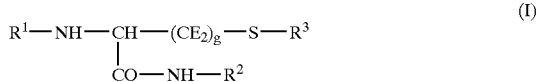

wherein in formula (I):

R¹ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each E represents, independently, a hydrogen atom or an alkyl group having 1–6 carbon atoms;

g stands for an integer of 0 to 5;

R² represents a hydrogen atom; an alkyl group selected from the group consisting of methyl, ethyl, propyl, isopropyl, n-butyl, isobutyl, sec-butyl, tert-butyl, n-amyl, sec-amyl, tert-amyl, isoamyl, n-hexyl, cyclohexyl, n-heptyl, n-octyl, 2-ethylhexyl, nonyl, isononyl, decyl, isodecyl, undecyl, lauryl, tridecyl, isotridecyl, myristyl, stearyl, isostearyl, oleyl, and behenyl; a hydroxyalkyl group having 1–22 carbon atoms; or a 3-alkoxy-2-hydroxypropyl group whose alkoxyl group has 1–22 carbon atoms, with the proviso that when $R^1$ represents a hydrogen atom or an acyl group having 2–3 carbon atoms, $R^2$ represents an alkyl group having 6–22 carbon atoms, a hydroxyalkyl group having 1–22 carbon atoms or a 3-alkoxy-2-hydroxypropyl group whose alkoxyl group has 1–22 carbon atoms;

$R^3$ represents an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms or a group represented by formula (1):

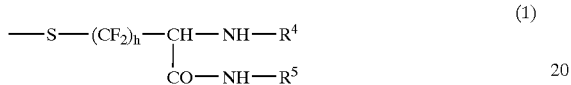

(1)

wherein in formula (1):

$R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each F represents, independently, a hydrogen atom or an alkyl group having 1–6 carbon atoms;

h stands for an integer of 0 to 5;

$R^5$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^4$ represents a hydrogen atom or an acyl group having 2–3 carbon atoms, $R^5$ represents an alkyl group having 6–22 carbon atoms, a hydroxyalkyl group having 1–22 carbon atoms or a 3-alkoxy-2-hydroxypropyl group whose alkoxyl group has 1–22 carbon atoms.

25. A cysteine or cystine compound represented by formula (I) or a salt thereof:

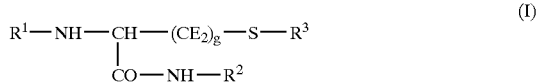

(I)

wherein in formula (I):

$R^1$ represents a hydrogen atom; an aminocarbonyl group; an acyl group selected from the group consisting of acetyl, propionyl, isopropionyl, n-butyryl, isobutyryl, sec-butyryl, tert-butyryl, n-valeryl, sec-valeryl, pivaloyl, isovaleryl, n-hexanoyl, cyclohexanoyl, n-heptanoyl, n-octanoyl, 2-ethylhexanoyl, nonanoyl, isononanoyl, decanoyl, isodecanoyl, undecanoyl, lauroyl, tridecanoyl, isotridecanoyl, myristoyl, palmitoyl, isopalmitoyl, stearoyl, isostearoyl, oleoyl, and docosanoyl; an alkyl group having 1–22 carbon atoms; a hydroxyalkyl group having 1–22 carbon atoms; or a 3-alkoxy-2-hydroxypropyl group whose alkoxyl group has 1–22 carbon atoms;

each E represents, independently, a hydrogen atom or an alkyl group having 1–6 carbon atoms;

g stands for an integer of 0 to 5;

$R^2$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^1$ represents a hydrogen atom or an acyl group having 2–3 carbon atoms, $R^2$ represents an alkyl group having 6–22 carbon atoms, a hydroxyalkyl group having 1–22 carbon atoms or a 3-alkoxy-2-hydroxypropyl group whose alkoxyl group has 1–22 carbon atoms;

$R^3$ represents an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms or a group represented by formula (1):

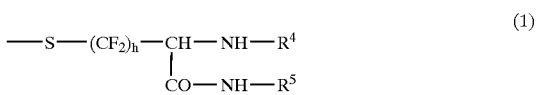

(1)

wherein in formula (1):

$R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each F represents, independently, a hydrogen atom or an alkyl group having 1–6 carbon atoms;

h stands for an integer of 0 to 5;

$R^5$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^4$ represents a hydrogen atom or an acyl group having 2–3 carbon atoms, $R^5$ represents an alkyl group having 6–22 carbon atoms, a hydroxyalkyl group having 1–22 carbon atoms or a 3-alkoxy-2-hydroxypropyl group whose alkoxyl group has 1–22 carbon atoms.

26. A cysteine or cystine compound represented by formula (I) or a salt thereof:

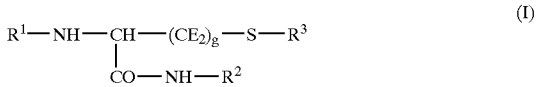

(I)

wherein in formula (I):

$R^1$ represents a hydrogen atom; an aminocarbonyl group; an acyl group selected from the group consisting of acetyl, propionyl, isopropionyl, n-butyryl, isobutyryl, sec-butyryl, tert-butyryl, n-valeryl, sec-valeryl, pivaloyl, isovaleryl, n-hexanoyl, cyclohexanoyl, n-heptanoyl, n-octanoyl, 2-ethylhexanoyl, nonanoyl, isononanoyl, decanoyl, isodecanoyl, undecanoyl, lauroyl, tridecanoyl, isotridecanoyl, myristoyl, and docosanoyl; an alkyl group having 1–22 carbon atoms; a hydroxyalkyl group having 1–22 carbon atoms; or a 3-alkoxy-2-hydroxypropyl group whose alkoxyl group has 1–22 carbon atoms;

each E represents, independently, a hydrogen atom or an alkyl group having 1–6 carbon atoms;

g stands for an integer of 0 to 5;

$R^2$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^1$ represents a hydrogen atom or an acyl group having 2–3 carbon atoms, $R^2$ represents an alkyl group having 6–22 carbon atoms, a hydroxyalkyl group having 1–22 carbon atoms or a 3-alkoxy-2-hydroxypropyl group whose alkoxyl group has 1–22 carbon atoms;

$R^3$ represents an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms or a group represented by formula (1):

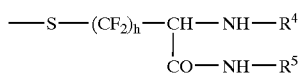

wherein in formula (1):

$R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each F represents, independently, a hydrogen atom or an alkyl group having 1–6 carbon atoms;

h stands for an integer of 0 to 5;

$R^5$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^4$ represents a hydrogen atom or an acyl group having 2–3 carbon atoms, $R^5$ represents an alkyl group having 6–22 carbon atoms, a hydroxyalkyl group having 1–22 carbon atoms or a 3-alkoxy-2-hydroxypropyl group whose alkoxyl group has 1–22 carbon atoms.

27. A cysteine or cystine compound represented by formula (I) or a salt thereof:

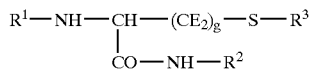

wherein in formula (I):

$R^1$ represents a hydrogen atom; an aminocarbonyl group; an acyl group selected from the group consisting of acetyl, propionyl, isopropionyl, n-butyryl, isobutyryl, sec-butyryl, tert-butyryl, n-valeryl, sec-valeryl, pivaloyl, isovaleryl, n-hexanoyl, cyclohexanoyl, n-heptanoyl, n-octanoyl, 2-ethylhexanoyl, nonanoyl, isononanoyl, decanoyl, isodecanoyl, undecanoyl, lauroyl, tridecanoyl, isotridecanoyl, myristoyl, palmitoyl, isopalmitoyl, stearoyl, isostearoyl, oleoyl, and docosanoyl; an alkyl group having 1–22 carbon atoms; a hydroxyalkyl group having 1–22 carbon atoms; or a 3-alkoxy-2-hydroxypropyl group whose alkoxyl group has 1–22 carbon atoms;

each E represents, independently, a hydrogen atom or an alkyl group having 1–6 carbon atoms;

g stands for an integer of 0 to 5;

$R^2$ represents an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^1$ represents a hydrogen atom or an acyl group having 2–3 carbon atoms, $R^2$ represents an alkyl group having 6–22 carbon atoms, a hydroxyalkyl group having 1–22 carbon atoms or a 3-alkoxy-2-hydroxypropyl group whose alkoxyl group has 1–22 carbon atoms;

$R^3$ represents a hydrogen atom, an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms or a group represented by formula (1):

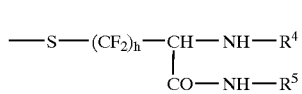

wherein in formula (1):

$R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each F represents, independently, a hydrogen atom or an alkyl group having 1–6 carbon atoms;

h stands for an integer of 0 to 5;

$R^5$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^4$ represents a hydrogen atom or an acyl group having 2–3 carbon atoms, $R^5$ represents an alkyl group having 6–22 carbon atoms, a hydroxyalkyl group having 1–22 carbon atoms or a 3-alkoxy-2-hydroxypropyl group whose alkoxyl group has 1–22 carbon atoms.

28. A cysteine or cystine compound represented by formula (I) or a salt thereof:

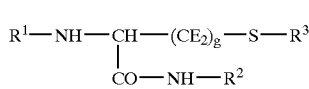

wherein in formula (I):

$R^1$ represents a hydrogen atom; an aminocarbonyl group; an acyl group selected from the group consisting of acetyl, propionyl, isopropionyl, n-butyryl, isobutyryl, sec-butyryl, tert-butyryl, n-valeryl, sec-valeryl, pivaloyl, isovaleryl, n-hexanoyl, cyclohexanoyl, n-heptanoyl, n-octanoyl, 2-ethylhexanoyl, nonanoyl, isononanoyl, decanoyl, isodecanoyl, undecanoyl, lauroyl, tridecanoyl, isotridecanoyl, myristoyl, and docosanoyl; an alkyl group having 1–22 carbon atoms; a hydroxyalkyl group having 1–22 carbon atoms; or a 3-alkoxy-2-hydroxypropyl group whose alkoxyl group has 1–22 carbon atoms;

each E represents, independently, a hydrogen atom or an alkyl group having 1–6 carbon atoms;

g stands for an integer of 0 to 5;

$R^2$ represents an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^1$ represents a hydrogen atom or an acyl group having 2–3 carbon atoms, $R^2$ represents an alkyl group having 6–22 carbon atoms, a hydroxyalkyl group having 1–22 carbon atoms or a 3-alkoxy-2-hydroxypropyl group whose alkoxyl group has 1–22 carbon atoms;

$R^3$ represents a hydrogen atom, an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms or a group represented by formula (1):

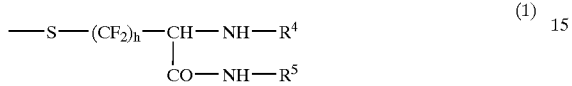

wherein in formula (1):

$R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each F represents, independently, a hydrogen atom or an alkyl group having 1–6 carbon atoms;

h stands for an integer of 0 to 5;

$R^5$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^4$ represents a hydrogen atom or an acyl group having 2–3 carbon atoms, $R^5$ represents an alkyl group having 6–22 carbon atoms, a hydroxyalkyl group having 1–22 carbon atoms or a 3-alkoxy-2-hydroxypropyl group whose alkoxyl group has 1–22 carbon atoms.

29. A cysteine or cystine compound represented by formula (I) or a salt thereof:

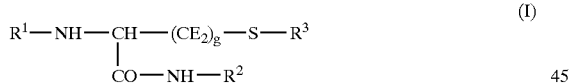

wherein in formula (I):

$R^1$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each E represents, independently, a hydrogen atom or an alkyl group having 1–6 carbon atoms;

g stands for an integer of 0 to 5;

$R^2$ represents an alkyl group selected from the group consisting of methyl, ethyl, propyl, isopropyl, n-butyl, isobutyl, sec-butyl, tert-butyl, n-amyl, sec-amyl, tert-amyl, isoamyl, n-hexyl, cyclohexyl, n-heptyl, n-octyl, 2-ethylhexyl, nonyl, isononyl, decyl, isodecyl, undecyl, lauryl, tridecyl, isotridecyl, myristyl, stearyl, isostearyl, oleyl, and behenyl; a hydroxyalkyl group having 1–22 carbon atoms; or a 3-alkoxy-2-hydroxypropyl group whose alkoxyl group has 1–22 carbon atoms, with the proviso that when $R^1$ represents a hydrogen atom or an acyl group having 2–3 carbon atoms, $R^2$ represents an alkyl group having 6–22 carbon atoms, a hydroxyalkyl group having 1–22 carbon atoms or a 3-alkoxy-2-hydroxypropyl group whose alkoxyl group has 1–22 carbon atoms;

$R^3$ represents a hydrogen atom, an aminocarbonyl group, an acyl group having 2–22 carbon atoms, an alkyl group having 1–22 carbon atoms, a hydroxyalkyl group having 1–22 carbon atoms, a 3-alkoxy-2-hydroxypropyl group whose alkoxyl group has 1–22 carbon atoms or a group represented by formula (1):

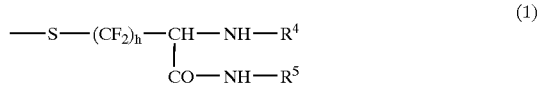

wherein in formula (1):

$R^4$ represents a hydrogen atom, an aminocarbonyl group, an acyl group having 2–22 carbon atoms, an alkyl group having 1–22 carbon atoms, a hydroxyalkyl group having 1–22 carbon atoms or a 3-alkoxy-2-hydroxypropyl group whose alkoxyl group has 1–22 carbon atoms;

each F represents, independently, a hydrogen atom or an alkyl group having 1–6 carbon atoms;

h stands for an integer of 0 to 5;

$R^5$ represents a hydrogen atom, an alkyl group having 1–22 carbon atoms, a hydroxyalkyl group having 1–22 carbon atoms or a 3-alkoxy-2-hydroxypropyl group whose alkoxyl group has 1–22 carbon atoms, with the proviso that when $R^4$ represents a hydrogen atom or an acyl group having 2–3 carbon atoms, $R^5$ represents an alkyl group having 6–22 carbon atoms, a hydroxyalkyl group having 1–22 carbon atoms or a 3-alkoxy-2-hydroxypropyl group whose alkoxyl group has 1–22 carbon atoms.

* * * * *